United States Patent
Dattelbaum et al.

(10) Patent No.: US 8,529,740 B2
(45) Date of Patent: Sep. 10, 2013

(54) ELECTROCHEMICAL APPARATUS COMPRISING MODIFIED DISPOSABLE RECTANGULAR CUVETTE

(75) Inventors: Andrew M Dattelbaum, Los Alamos, NM (US); Gautam Gupta, Los Alamos, NM (US); David E Morris, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 220 days.

(21) Appl. No.: 12/916,085

(22) Filed: Oct. 29, 2010

(65) Prior Publication Data

US 2012/0103807 A1    May 3, 2012

(51) Int. Cl.
*G01N 27/403* (2006.01)
(52) U.S. Cl.
USPC ........................................................ 204/400
(58) Field of Classification Search
USPC ............... 204/400, 409–412, 403.01, 403.02, 204/286.1, 287, 242, 247, 255, 257, 232, 204/234, 237; 422/82.01–82.03; 324/437, 324/450
See application file for complete search history.

(56) References Cited

U.S. PATENT DOCUMENTS

| | | | | |
|---|---|---|---|---|
| 4,133,734 | A | * | 1/1979 | Polak et al. .................. 204/404 |
| 4,230,537 | A | * | 10/1980 | Delente et al. ................ 205/778 |
| 4,310,400 | A | * | 1/1982 | Mark et al. .................... 204/412 |
| 8,115,922 | B2 | | 2/2012 | Webster et al. |

OTHER PUBLICATIONS

Princeton Applied Research Product Catalog, pp. 1-22, 2012, (the products in this catalog were on sale prior to applicant's invention).
STARNA, The Spectroscopy Specialists, Quartz and Glass Cells for: Spectrophotometers, Fluorometers, Colorimeters, Laser Applications, 2012 Catalog and Price List, pp. 1-44, Aug. 2012, (the products in this catalog were on sale prior to applicant's invention).

* cited by examiner

*Primary Examiner* — Alex Noguerola
(74) *Attorney, Agent, or Firm* — Samuel L. Borkowsky

(57) ABSTRACT

Electrochemical apparatus includes a disposable rectangular cuvette modified with at least one hole through a side and/or the bottom. Apparatus may include more than one cuvette, which in practice is a disposable rectangular glass or plastic cuvette modified by drilling the hole(s) through. The apparatus include two plates and some means of fastening one plate to the other. The apparatus may be interfaced with a fiber optic or microscope objective, and a spectrometer for spectroscopic studies. The apparatus are suitable for a variety of electrochemical experiments, including surface electrochemistry, bulk electrolysis, and flow cell experiments.

7 Claims, 9 Drawing Sheets

ELECTROCHEMICAL APPARATUS COMPRISING MODIFIED DISPOSABLE RECTANGULAR CUVETTE

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to apparatus for electrochemistry that include a modified disposable rectangular cuvette.

BACKGROUND OF THE INVENTION

Commercially available electrochemical apparatus are expensive. A quartz cell typically costs more than $1000. Cells made from poly(tetrafluoroethylene) or from an acrylic polymer may cost more than $230 each. Those used for bulk electrolysis ($800), for flow ($850) and for general electrochemistry ($20-$200) are also too expensive to be considered disposable. They must be cleaned after each experiment. Electrochemistry is a sensitive technique, and residual chemicals from prior experiments, and even from a cleaning, may contaminate a later experiment performed in the same cell. In addition, especially in academia, the high cost may result in a laboratory being able to afford only a small number of cells that are likely shared amongst several researchers who all must have access to them. This limits productivity.

In addition to their high cost, most electrochemical apparatus lack the flexibility of being useful for both solution electrochemistry and surface electrochemistry. An electrochemical cell that is generally useful for solution electrochemistry cannot easily be modified for surface electrochemistry experiments. In addition, traditional electrochemical apparatus have limited capacity to interface with optical fibers, microscopes, spectrometers, and other optical instrumentation.

An inexpensive electrochemical apparatus that can be modified easily for solution and surface electrochemistry, and that can also interface with optical instrumentation, is desirable.

SUMMARY OF THE INVENTION

In accordance with the purposes of the invention, as embodied and broadly described herein, the invention includes an electrochemical cell that comprises a disposable rectangular cuvette having four rectangular sides, a top end, and a bottom end. The top end of the cuvette is open. There is at least one hole through the cuvette. For example, there may be a hole in a rectangular side. There may be a hole in the bottom end. There may be a hole in a side and also in the bottom end. There may be a hole in a rectangular side and a hole in the opposite rectangular side. There may be a plurality of holes in one side. There may be a plurality of holes in one side, and a hole in the bottom end.

The invention also includes an electrochemical apparatus capable of interfacing with optical instrumentation through a side of an electrochemical cell. The cell includes a disposable rectangular cuvette with four rectangular sides, a top end and a bottom end. The top end is open. The bottom end is closed. There is a side hole through a rectangular side of the cuvette. A gasket surrounds the side hole. The gasket is compressed in between the cuvette and a working electrode. A cap seals the open top end of the cuvette. Holes thorough the cap are provided for insertion of a reference electrode, a counter electrode, and if desired, a gas inlet and outlet. A clamp made of two plates and a clamping means compresses the apparatus so the gaskets can provide leak-proof seals. There is a hole in the side plate nearest the working electrode that aligns with the side hole in the cuvette. If the working electrode is transparent, light from an optical fiber may be directed through the hole in the plate, through the working electrode, and into the cuvette. Light from inside the cuvette may then be transmitted back through the working electrode and back through the optical fiber (or through an additional optical fiber) to a spectrometer where it may be analyzed to provide information about the electrochemistry taking place inside the cuvette during an experiment.

The invention also includes an electrochemical apparatus capable of interfacing with optical instrumentation through the bottom of an electrochemical cell. The apparatus comprises an electrochemical cell and a cell holder that also acts as a stand for the apparatus. The cell includes a disposable rectangular cuvette having an open top end, a bottom end, and four rectangular sides. The holder includes a top rectangular plate having a groove that mates with the open top end of the cuvette. The groove defines a perimeter for a plurality of holes through the top plate inside the perimeter. The top rectangular plate includes four corners and a hole through the plate at each corner for receiving a screw. The holder also includes a bottom rectangular plate for supporting the bottom end of the cuvette. The bottom plate also has four corners and a threaded hole at each corner for receiving a screw. When the cuvette is in position in between the two plates and the groove in the top plate mates with the open top end of the cuvette, the top plate and the bottom plate are parallel to each another and a hole through the center of bottom plate overlaps a hole drilled through the bottom end of the cuvette, and the holes through the corners of the plates overlap so that a screw may pass through holes at the corners of both plates. A bottom gasket surrounds the hole in the bottom end of the cuvette. A flat electrode is positioned in between the bottom gasket and the bottom plate. A nut fastens each screw to the top plate. During fastening, the top open end of the cuvette is pressed against the groove in the top plate, and the bottom gasket provides a leak-proof seal with the bottom plate. A reference electrode and a counter electrode fit through holes within the perimeter in the top plate and extend into the cuvette. If desired, a gas inlet and outlet are also provided through holes within the perimeter of the top plate.

The invention also includes an electrochemical apparatus having an electrochemical cell comprising two disposable rectangular cuvettes and a clamp. Each cuvette has four rectangular sides and an open top end. Each cuvette also has a side hole through a rectangular side of the cuvette. The two cuvettes are positioned side-by-side such that the sides with the side hole are adjacent and the side holes are in alignment with each other. A gasket surrounds each side hole. An ion-permeable membrane is positioned in between the two gaskets. A cap seals the open top end of each cuvette. Holes through the caps are provided for a reference electrode, a counter electrode, and if desired, a gas inlet and outlet. A clamp is provided for maintaining the side-by-side position of the two cuvettes, and provides compression such that the gaskets provide leak-proof seals with the cuvettes and the membrane in between the gaskets.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings:

FIG. 9b shows an image of the assembled apparatus of FIG. 9a.

FIG. 10b shows an image of the assembled apparatus of FIG. 10a.

DETAILED DESCRIPTION

The invention is concerned with electrochemistry and more particularly with apparatus for performing electrochemistry. Each electrochemical apparatus includes an electrochemical cell having one or more disposable rectangular cuvettes. Cuvettes are commercially available containers. They are generally made of glass or plastic and are inexpensive, costing only a few cents apiece, and therefore they are disposable. Cuvettes are typically used for spectroscopic analysis. They are filled with a solution and then positioned in a spectrometer such as a UV-VIS spectrometer. Sometimes, a cuvette with a blank solution is used, along with a cuvette with a soluble sample solution containing an absorbing material, and light is used to interrogate the sample and provide information about the concentration of the absorbing material.

In the present invention, the rectangular cuvette is modified with a hole or holes. The modified cuvette is then used as part of an electrochemical apparatus. Because the cuvettes are inexpensive, they can be disposed of after an experiment. This minimizes the possibility of contaminating an electrochemical experiment with residual chemicals from a prior experiment or cleaning procedure.

An aspect of the invention relates to flexibility in the types of electrochemistry that may be performed with the electrochemical apparatus employing these modified rectangular cuvettes. For example, apparatus of this invention may be used to perform electrochemistry in solution. An embodiment apparatus may be used to perform electrochemistry on surfaces. An embodiment apparatus may useful for bulk electrolysis experiments. An embodiment apparatus may be used in an academic laboratory for studying many important chemical and biological problems. For example, an embodiment apparatus may be used for studying the corrosion of paint or metal for the automotive industry. An embodiment apparatus may be used for studying the corrosion of metals or biofilm formation for the shipping industry. An embodiment apparatus may be used for studying fuel cells and batteries.

Each embodiment electrochemical apparatus of this invention includes a disposable rectangular cuvette that has been modified with one or more holes through the cuvette.

In an embodiment, there is a hole through a rectangular side of the cuvette.

In another embodiment, there is a hole through the bottom of the cuvette.

In yet another embodiment, there is a hole through a rectangular side and also a hole through the bottom of the cuvette.

In still another embodiment, there is a hole through a rectangular side and another hole through the opposite side.

In another embodiment, there is a plurality of holes through a rectangular side of the cuvette.

In another embodiment, there is a plurality of holes through a rectangular side of the cuvette and a hole through the bottom of the cuvette.

In another embodiment, there is a hole through a rectangular side, a hole through an opposing rectangular side, and a hole through the bottom of the cuvette.

The invention is concerned with the above modified disposable rectangular cuvettes. The invention is also with electrochemical apparatus that employ these modified cuvettes. The electrochemical apparatus of the present invention include electrochemical cells having at least one of these cuvettes. Each modified cuvette for a cell is fitted with a cap for the top of the cuvette. Each cell also includes a reference electrode and a counter electrode. These electrodes fit through holes in the cap so they come in contact with an electrolyte solution inside the cuvette. Each cell also includes a working electrode. Sometimes, the working electrode is a flat electrode near a hole in a rectangular side or near a hole in the bottom of the cuvette. Sometimes, the working electrode fits through a hole in the cap (in this case, the working electrode could be a wire mesh). The electrochemical apparatus is also provided with a holder that functions as a stand so that the apparatus doesn't tip over.

An embodiment apparatus useful for experiments related to surface electrochemistry employs an embodiment rectangular cuvette with a hole through a rectangular side, a gasket around the side hole, and a flat substrate compressed against the gasket. The flat substrate functions as the working electrode. If the substrate is transparent, the apparatus may be interfaced with optical instrumentation for interrogating the electrochemistry at the surface of the substrate. The optical instrumentation sends light through the substrate and into the cell, and light from inside the cell passes through the substrate and to the optical instrumentation for analysis. The optical instrumentation may be a microscope objective for direct, magnified observation of the substrate.

For various embodiment apparatus of this invention, fiber optics may be used with a variety of spectroscopic equipment such as, but not limited to, a UV-visible spectrometer, an FT-IR spectrometer, a fluorescence spectrometer, and the like. These and other types of spectroscopic instruments can be used for characterizing the electrochemical reactions at the working electrode surface or inside the cuvette(s) in detail as they occur. An embodiment apparatus including a cuvette with a hole in the bottom may be interfaced with such optical instrumentation. In an embodiment employing a rectangular cuvette modified with a hole through the bottom of the cuvette, a gasket (or other sealing means) surrounds the hole and a transparent or translucent planar working electrode is compressed against the gasket. A fiber optic cable or microscope objective is positioned near or sealed against the planar working electrode to study electrochemical events at the electrode surface. Any sealing means for sealing the electrode that does not interfere with the electrochemistry or contaminate the electrochemical solution in the cuvette may be used. An o-ring of an appropriate material, or a plastic cap with a hole and a suitable fitting for sealing to a fiber optic cable, may be used for sealing the fiber optic to the bottom of the working electrode. Immersion oil may be used to interface the working electrode and a microscope objective. During an experiment, light is transmitted from the spectrometer through the fiber optic or objective into the cuvette, and light from inside the cuvette travels back to the spectrometer potentially through the fiber optic or objective. Analysis of the light may provide information about the experiment to support or in addition to the electrochemical data.

An embodiment electrochemical apparatus useful as a fuel cell and for performing bulk electrolysis may include two cuvettes, each with a side hole and positioned with their side holes aligned. Sealing members (gaskets, for example) surround the side holes of each cuvette. The apparatus also may include an ion-permeable membrane in between the gaskets.

Each electrochemical apparatus is provided with an appropriate electrolyte solution inside the cuvette(s) prior to use. All of the apparatus can be assembled very easily.

The practice of the invention can be further understood with the accompanying FIGURES. Similar or identical structure is identified using identical callouts.

FIGS. 1 through 7 depict various embodiments of modified disposable rectangular cuvettes of the present invention.

Figure 1:
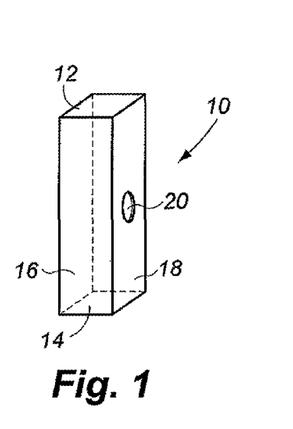
FIG. 1 shows a view of an embodiment modified rectangular cuvette of the present invention with a side hole through rectangular side.

FIG. 1 shows cuvette 10 including an open top end 12, a closed bottom end 14, and three unmodified rectangular sides 16 and one modified rectangular side 18 that has been modified with a hole 20 through the side.

Figure 2:
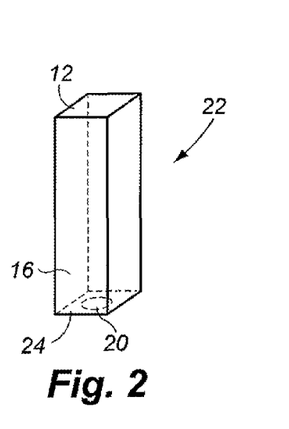
FIG. 2 shows a view of an embodiment modified rectangular cuvette of the present invention with a bottom hole.

FIG. 2 shows cuvette 22 including open top end 12, four rectangular sides 16, and a bottom end 24 with a hole 20 through the bottom end.

Figure 3:
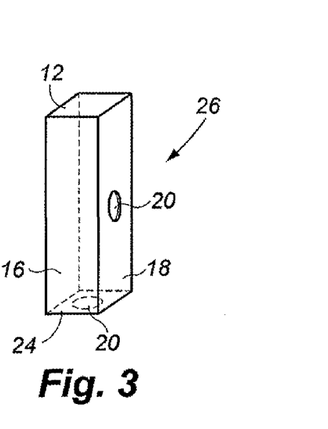
FIG. 3 shows a view of an embodiment modified rectangular cuvette of the present invention with a side hole through a rectangular side and a bottom hole.

FIG. 3 shows cuvette 26 including open top end 12, bottom end 24 with a hole through the bottom end, three rectangular sides 16 and a fourth rectangular side 18 with a hole through the side.

Figure 4:
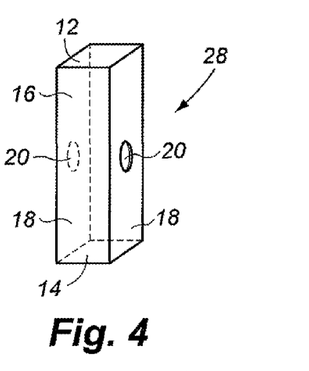
FIG. 4 shows a view of an embodiment modified rectangular cuvette of the present invention with side holes through opposite rectangular sides.

FIG. 4 shows cuvette 28 including open top end 12, closed bottom end 14, two rectangular sides 16, and two rectangular sides 18 wherein the two rectangular sides 18 include a hole 20 through each side, and the two sides with the holes are opposite each other. In an embodiment, these holes are aligned with each other. In another embodiment, the holes are not aligned with each other.

Figure 5:
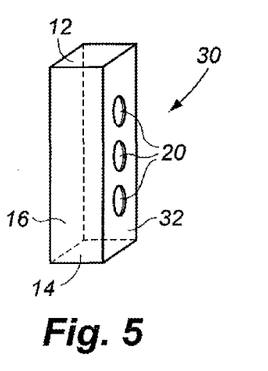
FIG. 5 shows a view of an embodiment modified rectangular cuvette of the present invention with three side holes through a rectangular side.

FIG. 5 shows cuvette 30 including an open top end 12, a closed bottom end 14, three rectangular sides 16, and a rectangular side 32 with a plurality of holes through the side. In the embodiment shown in FIG. 5, there are three holes through side 32. In other embodiments, there may be greater than 3 holes through side 32.

Figure 6:
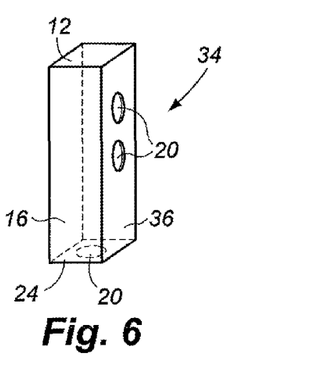
FIG. 6 shows a view of an embodiment modified rectangular cuvette of the present invention with two side holes through a rectangular side, and a hole through the bottom.

FIG. 6 shows cuvette 34 includes an open top 12, a bottom 24 with hole 20 through the bottom, three rectangular sides 16, and rectangular side 36 with two holes 20 through side 36.

Figure 7:
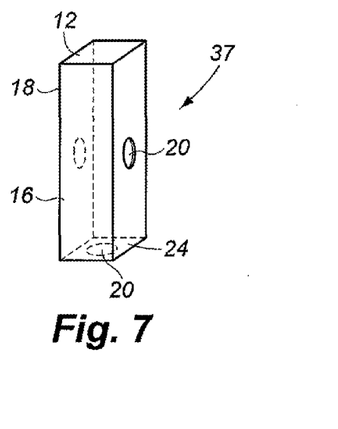
FIG. 7 shows a view of an embodiment modified rectangular cuvette of the present with a side hole through a rectangular side, another side hole through the opposite rectangular side, and a hole through the bottom.

FIG. 7 shows cuvette 37 which includes an open top 12, a bottom 24 with hole 20 through the bottom. Cuvette 37 includes two rectangular sides 16, and two rectangular sides 18 that are opposite each other with a hole through each.

Figure 8:
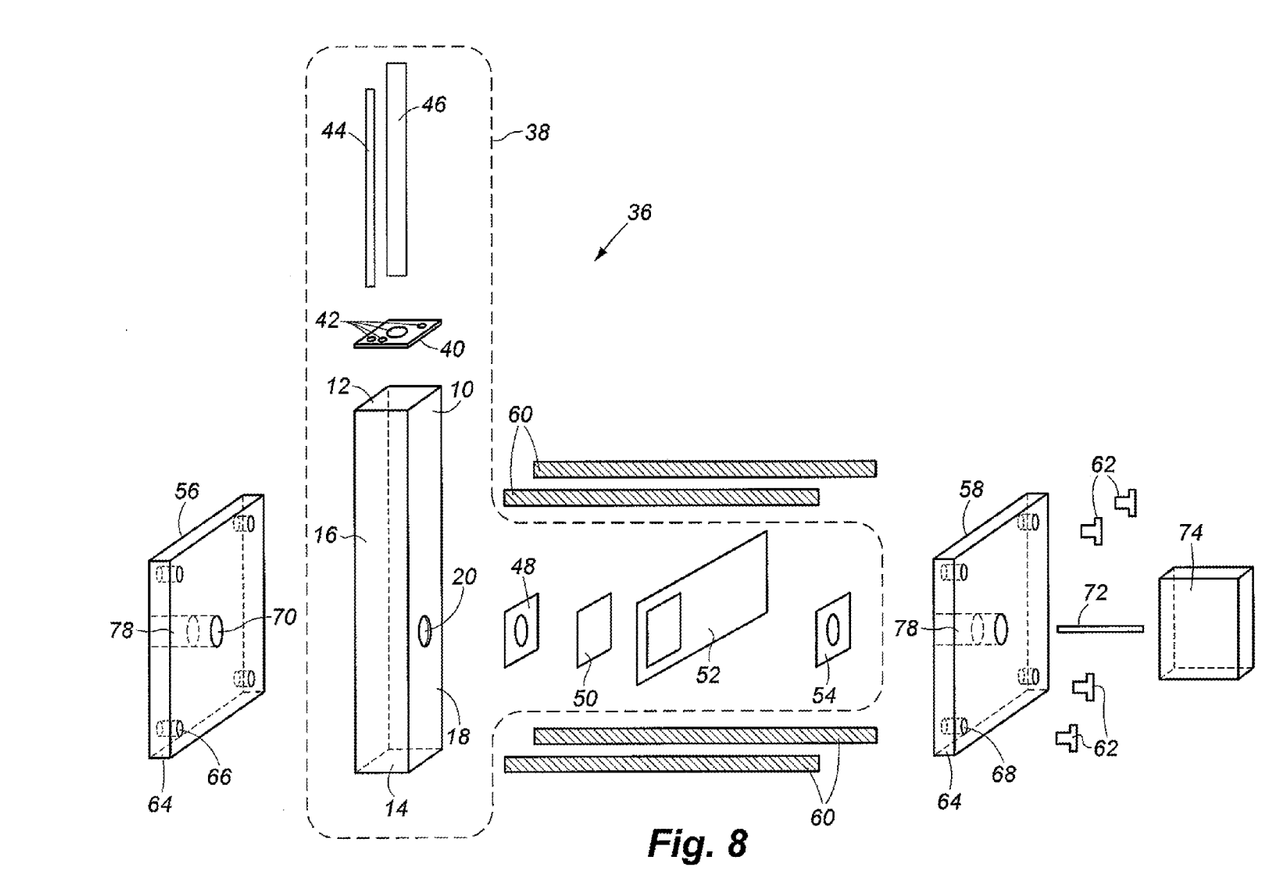
FIG. 8 shows an exploded view of an embodiment electrochemical apparatus employing the modified rectangular cuvette shown in FIG. 1.

FIG. 8 shows an embodiment electrochemical apparatus 36, which is useful for performing solution or surface electrochemistry. Apparatus 36 includes an electrochemical cell 38. Cell 38 includes disposable rectangular cuvette 10 (see FIG. 1) having open top 12 end, closed bottom end 14, three rectangular sides 16, and fourth rectangular side 18 with a hole 20 through the side. Cap 40 fits open end 12 of cuvette 10. Reference electrode 44 and counter electrode 46 fit through holes 42 in cap 40 and extend inside cuvette 10. Although four holes 42 of different sizes in cap 40 are provided, it should be understood that the number and size of these holes is variable and will depend on, amongst other things, the sizes of reference electrode 44 and counter electrode 46. One of the holes may be used as a gas inlet for gas purging. Another hole may be provided for a reactive gas, as needed. These choices depend on the experimenter's needs. When a gas is used or generated during a reaction, a hole in cap 40 would relieve the gas pressure. O-rings may be wrapped around the electrodes to suspend them and prevent them from falling to the bottom of the cuvette.

Electrochemical cell 38 of apparatus 36 includes gasket 48, which surrounds hole 20 in cuvette 10 and seals side 18 to substrate/working electrode 50 (i.e. the flat substrate functions as the working electrode for the cell). Substrate/working electrode 50 also seals against a current collector 52. Gasket 54 seals current collector 52 to a portion of a cell holder that consists of a first side plate 56 and second side plate 58 and a holding mechanism that attaches the plates to each other. The holding mechanism in this embodiment includes screws 60 and nuts 62 as shown in FIG. 7. First side plate 56 and second side plate 58 each have four corners 64 each and a threaded hole 66 at each corner. Each screw 60 is threaded into hole 66 in first side plate 56 and passes through an unthreaded corner hole 68 in second plate 58 and is fastened with nuts 62, which aligns first plate 56 with second plate 58 in a parallel relationship. When assembled, the nuts are tightened sufficiently such that the gaskets 48 and 54 provide seals with the cuvette 10, working electrode 50, and current collector 52 to prevent leakage of electrolyte from the cell during operation. Current collector 52 may be attached to first plate 56, to second plate 58, or to working electrode 50 prior to conducting an experiment.

A centrally located hole 70 in second side plate 58 aligns with hole 20 in cuvette 10 when the apparatus 36 is assembled so that light from a fiber optic cable 72, for example, may provide light through hole 70 and into cuvette 10 provided substrate/working electrode 50 is transparent or translucent. Light transmitted from inside the cuvette may exit through hole 20, and back through substrate/working electrode 50, and back through fiber optic cable 72 to optical instrumentation 74 (spectrometers, etc.). Analysis of the light provides information about the electrochemistry taking place during an experiment.

Instead of the fiber optic cable 72 and spectrometer 74, a microscope objective may be used for observing substrate/ working electrode during an experiment. Optionally, a portion 78 of first plate 56 is removable to accommodate a large microscope objective.

Figure 9A:
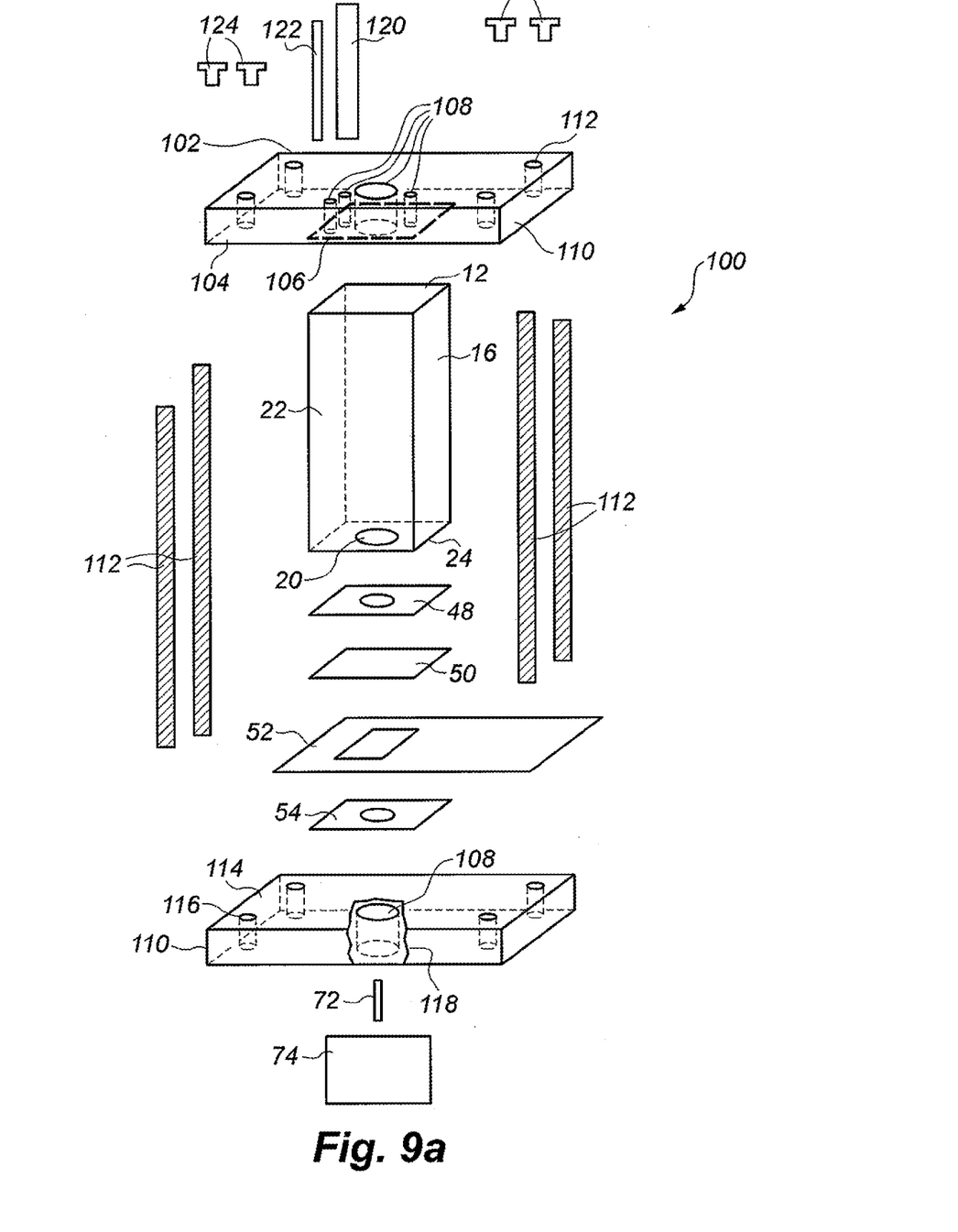
FIG. 9a shows an exploded view of an embodiment apparatus that is capable of interfacing with optical instrumentation through a bottom hole in a rectangular cuvette.

Another embodiment electrochemical apparatus of the present invention is shown in FIG. 9a. Electrochemical apparatus 100 includes disposable rectangular cuvette 22 (see FIG. 2). Cuvette 22 has an open top end 12, four rectangular sides 16, and a bottom end 24 with a hole 20 through the bottom end 24. In practice, cuvette 22 is a commercially available, disposable, glass or plastic, rectangular cuvette that has been modified by drilling a hole through the bottom of the cuvette, or providing the hole by some other means.

Apparatus 100 also includes a top rectangular plate 102 having a bottom side 104 with a groove 106 that mates with the top end 12 of cuvette 22. Groove 106 defines a perimeter for holes 108 through the plate. Each of the holes 108 is inside the perimeter. The embodiment shown in FIG. 2 provides four holes 108 of different sizes, the largest in the center of the top plate 102. The other holes 108 are off to a side of the central hole but still within the perimeter defined by groove 106. It should be understood that the number and size of these holes is variable. For example, electrodes pass through these holes. A wide electrode requires a hole wide enough to receive the electrode. If gas purging is desired, holes for a gas inlet and outlet are needed. A reactive gas may also be desired, so a hole for such as gas would be available if needed. It would be up to the experimenter to determine whether a gas is desired. When a gas is used, or is generated during a reaction, a hole within the perimeter may be used as a gas outlet to relieve gas pressure inside the cell. Top plate 102 of apparatus 100 includes four corners 110 and a corner hole 112 at each corner through the plate for receiving a screw 112.

Apparatus 100 also includes a bottom rectangular plate 114 that supports the bottom end 24 of the cuvette 22. The bottom plate 114 also has four corners 110 and a threaded hole 116 at each corner for threaded engagement with a screw 112. Each screw 112 engages a threaded hole 116 in the bottom plate 114 and passes through a corner hole in the top plate. When assembled, the top plate 102 is in a parallel relationship with the bottom plate 114 and groove 106 mates with the open top end 12 of cuvette 22. Also, a hole 108 in the center of the bottom plate overlaps the hole 20 in the bottom end 24 of cuvette 22. A fiber optic cable 72 may direct light through hole 20. The fiber optic cable 72 may also be interfaced with a spectrometer 74 for studying the electrochemistry taking place in cuvette 22 (for example, surface electrochemistry on working electrode 50) in detail as it occurs. Optionally, portion 118 of bottom plate 114 is removable for interfacing with a large microscope objective.

Apparatus 100 also includes a reference electrode 120 that fits through a hole inside the perimeter of the groove 106 in the top plate 102 and extends into the cuvette 22.

Apparatus 100 also includes a counter electrode 122 that fits through a hole inside the perimeter of the groove 106 in the top plate 102 and extends into the cuvette 22.

Apparatus 100 also includes a gasket 48 for sealing the bottom end 24 of the cuvette 22 to the working electrode 50. Apparatus 100 also includes current collector 52 adjacent substrate/working electrode 50. A gasket 54 between substrate/working electrode 50 and the bottom rectangular plate 114 seals the current collector with the bottom rectangular plate. A nut 124 for each screw 122 is used for fastening the top plate 102 to the bottom plate 114. When the plates are fastened, the top end 12 of cuvette 22 presses against the rectangular groove 106 of the top plate 102 and the gaskets 48 and 54 provide seals that prevent leakage of electrolyte from the electrochemical cell. An image of the assembled apparatus 100 is shown in FIG. 8b.

Figure 10A:
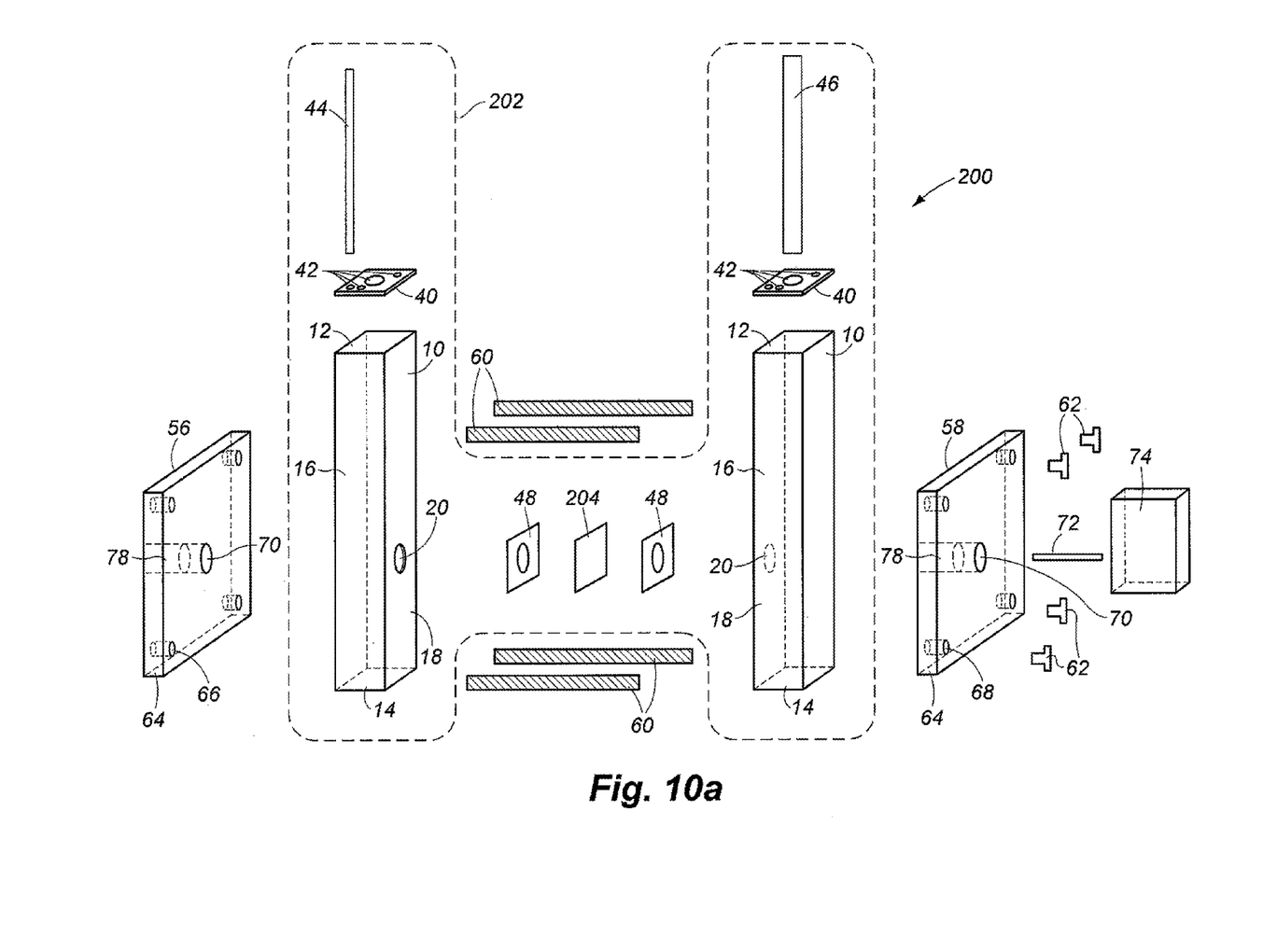
FIG. 10a shows an exploded view of an embodiment apparatus of the present invention that includes two rectangular cuvettes and an ion permeable membrane in between the cuvettes.

FIG. 10a shows an embodiment apparatus useful for bulk electrolysis experiments. Apparatus 200 includes an electrochemical cell 202 and a holder for the cell. Cell 202 includes two cuvettes 10. In practice, each cuvette 10 is a commercially available disposable glass or plastic rectangular cuvette modified by drilling a hole through a rectangular side 14. The two cuvettes 10 are positioned side-by-side so that a hole 20 in one of the cuvettes 12 aligns with the hole 20 in other cuvette 12. The cell includes two gaskets 48, one for surrounding each side hole and sealing against side 10 of each cuvette 12. The cell 202 also includes an ion-permeable membrane 204 in between the two gaskets 48. Each cuvette has a cap 42 that seals the open top end 12 and holes 42 in the cap 40 are provided for a reference electrode 44, a counter electrode 46, and optionally if desired, a gas inlet and outlet.

The electrochemical apparatus 200 also includes a holder consisting of a first rectangular plate 56 and a second rectangular plate 58 and a holding mechanism consisting of screws 60 and nuts 62. The holding mechanism has already been described for apparatus 36 shown in FIG. 7. The holder maintains the side-by-side position of the cuvettes and provides compression so that gaskets 48 form seals with cuvettes 10, membrane 204, and plates 56 and 58. An image of an assembled apparatus 200 is shown in FIG. 10b without the electrolyte solution.

Figure 11:
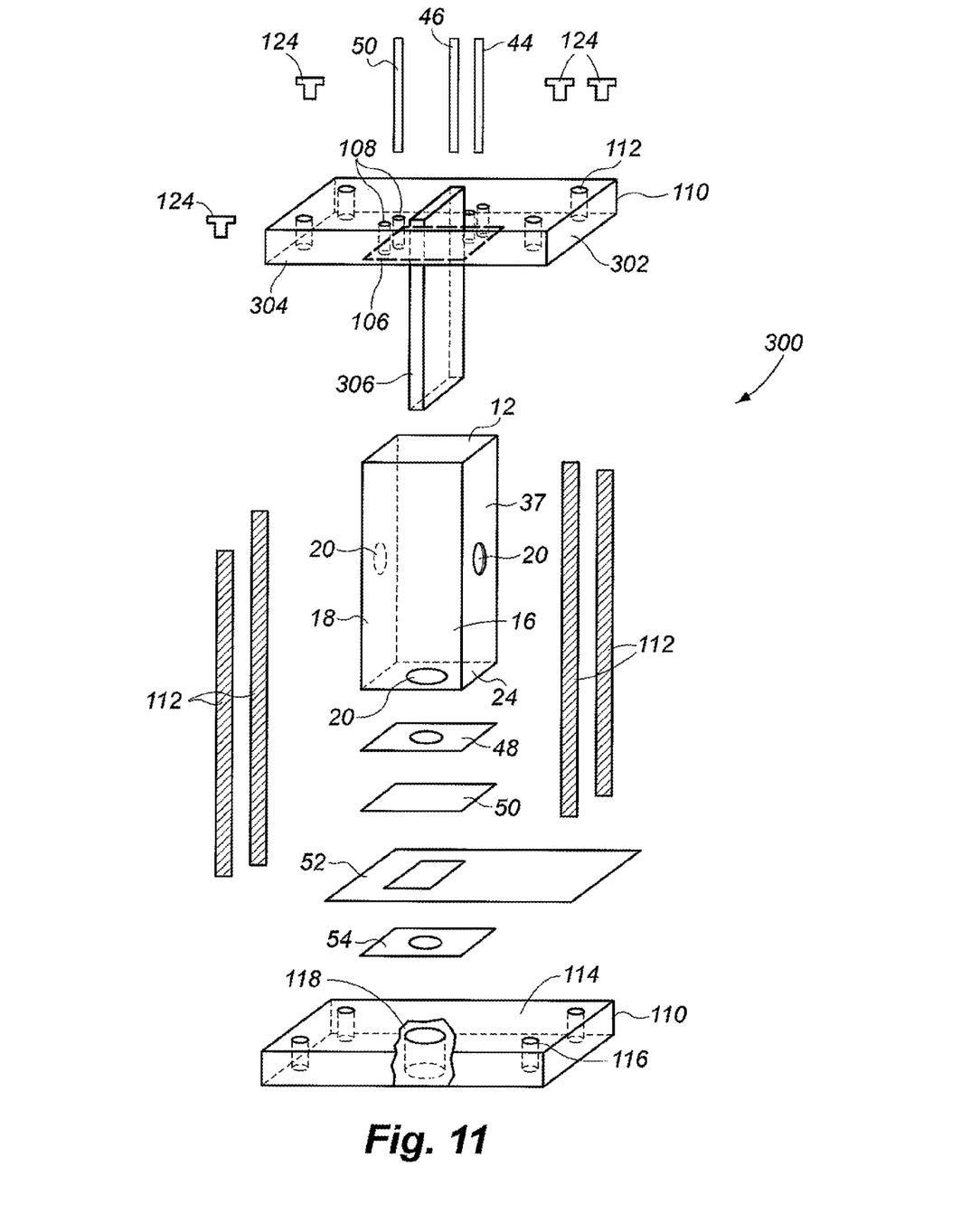
FIG. 11 shows an exploded view of an embodiment apparatus of the present invention useful for flow experiments.

FIG. 11 shows an embodiment apparatus 300 useful for flow cell experiments. This embodiment apparatus 300 includes cuvette 37 (see FIG. 7), which includes top end 12, bottom end 24 with a hole 20 through the bottom, two sides 16, and two sides 18 each having a hole through the side. In practice, cuvette 37 is prepared by drilling holes through opposite rectangular sides and also through the bottom of a commercially available glass or plastic disposable rectangular cuvette. The two side holes 20 of cuvette 37 allow liquid to flow into and out of cuvette 37.

Embodiment apparatus 300 includes a top rectangular plate 302 having a bottom side 304 with a groove 106 that mates with top end 12 of cuvette 37. Groove 106 defines a perimeter for holes 108 through the plate. Each of the holes 108 is inside the perimeter. A partition 306 is attached to the plate that extends inside cuvette 37 to separate cuvette 37 into two compartments but does not touch the bottom of the cuvette. The holes 108 in the perimeter provide entrances into both compartments when the apparatus 300 is assembled. The four holes 108 are of different sizes. It should be understood that the number and size of these holes is variable. Electrodes pass through these holes 108. In the embodiment shown, reference electrode 44 and counter electrode 46 pass through plate into one compartment. If gas purging is desired, holes for a gas inlet and outlet are needed. A reactive gas may also be desired, so a hole for such as gas would be available if needed. It would be up to the experimenter to determine whether a gas is desired. When a gas is used, or is generated during a reaction, a hole within the perimeter may be used as a gas outlet to relieve gas pressure inside the cell.

Top plate 302 includes four corners 110 and a corner hole 112 at each corner through the plate for receiving a screw 112. The embodiment shown in FIG. 11 has four screws.

Apparatus 300 also includes a bottom rectangular plate 114 that supports the bottom end 24 of the cuvette 37. The bottom plate 114 also has four corners 110 and a threaded hole 116 at each corner for threaded engagement with a screw 112. Each screw 112 engages a threaded hole 116 in the bottom plate 114 and passes through a corner hole in the top plate. When assembled, the top plate 302 is in a parallel relationship with the bottom plate 114 and groove 106 mates with the open top end 12 of cuvette 22, and partition 306 divides the cuvette into two compartments with space at the bottom for liquid to into one compartment from the other compartment. A hole in the center of the bottom plate overlaps the hole 20 in the bottom end 24 of cuvette 37. A fiber optic cable 72 may direct light through hole 20. There are also two holes 28 on the opposite sides of the cuvette to be used as an inlet and outlet, respectively, for fluid. The working electrode 50 will thus experience a regular flow of fluid from one side of the bather to the other, resulting in a flow cell. The fiber optic cable 72 may also be interfaced with a spectrometer 74 for studying the electrochemistry taking place in cuvette 22 (for example, surface electrochemistry on working electrode 50) in detail as it occurs. Optionally, portion 118 of bottom rectangular plate 114 is removable for interfacing with a large microscope objective.

Apparatus 300 also includes a reference electrode 120 that fits through a hole inside the perimeter of the groove 106 in the top plate 102 and extends into the cuvette 22. Apparatus 300 also includes a counter electrode 122 that fits through a hole inside the perimeter of the groove 106 in the top plate 102 and extends into the cuvette 22.

Gasket 48 seals the bottom end 24 of the cuvette 22 to the working electrode 50. Apparatus 100 also includes current collector 52 adjacent substrate/working electrode 50. A gasket 54 between substrate/working electrode 50 and the bottom rectangular plate 114 seals the current collector 52 with the bottom rectangular plate 114. A nut 124 for each screw 122 is used for fastening the top plate 102 to the bottom plate 114. When the plates are fastened, the top end 12 of cuvette 37 presses against the rectangular groove 106 of the top plate 102 and the gaskets 48 and 54 provide seals that prevent leakage of electrolyte from the electrochemical cell.

The embodiments above are intended as illustrative only, since numerous modifications and variations will be apparent to those skilled in the art. Several non-limiting examples below are provided to illustrate the operability of various embodiment electrochemical apparatus of this invention.

EXAMPLE 1

Cyclic Voltammetry

Figure 12:
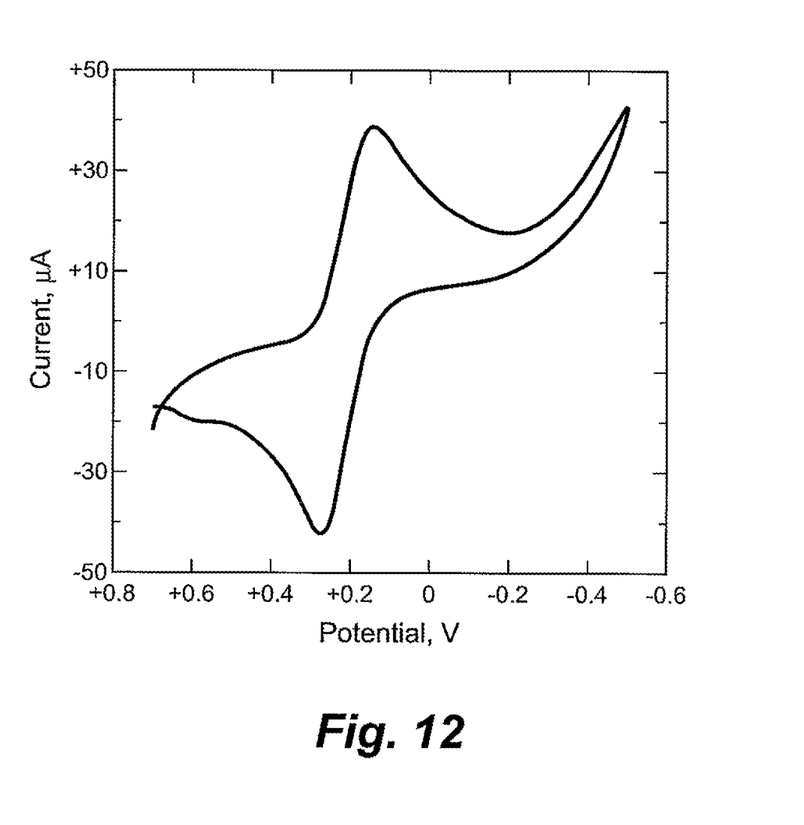
FIG. 12 shows results of a cyclic voltammogram using the apparatus of FIGS. 9a and 9b.

Electrochemical apparatus 100, shown in FIGS. 9a-b, was used to demonstrate a cyclic voltammetry experiment. The working electrode was a gold working electrode made of a gold coated glass slide. The gold working electrode was positioned at the bottom of the cuvette (apparatus 100, FIGS. 9a and 9b), although similar results were obtained with the working electrode positioned on the side of the cuvette (apparatus 36, FIG. 8). A silicone gasket with a 0.85 cm diameter hole drilled into the gasket was used to seal the working electrode (gold film) to the cuvette to prevent leakage. A 1 mM ferricyanide (1 ml; $[Fe^{III}(CN)_6]^{3-}$) solution was then added to the assembled cell. The $Fe^{III}/Fe^{II}$ redox couple is a standard electrochemically reversible redox system. A Ag/AgCl reference electrode and a platinum counter electrode were then inserted through the top of the electrochemical cell. A cyclic voltammogram collected on this system at a scan rate of 50 mV/s is shown in FIG. 12. The reversible electrochemical behavior between $Fe^{III}$ and $Fe^{II}$ was clearly observed and is consistent with similar results presented in the literature.

EXAMPLE 2

Formation of a Monolayer on an Electrode

Figure 13:
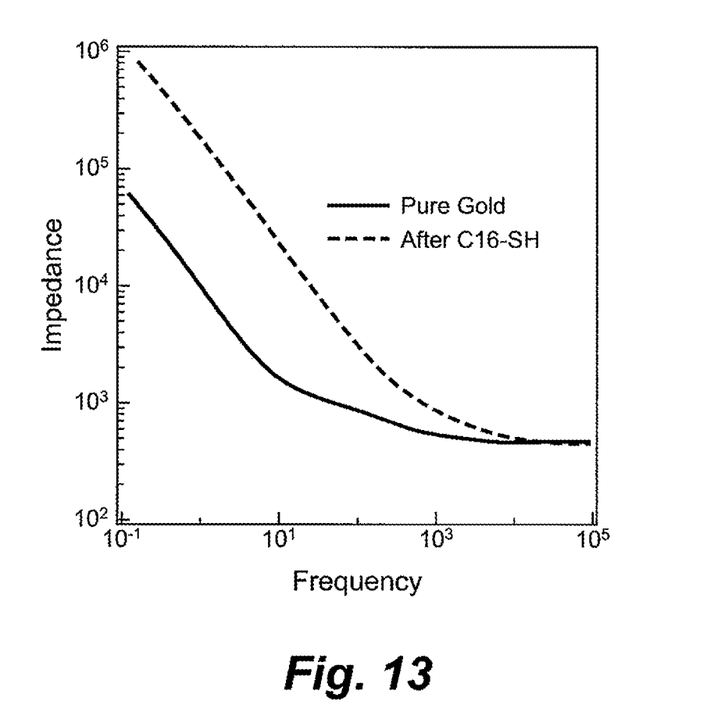
FIG. 13 shows results of formation of a monolayer on an electrode surface of an embodiment apparatus.

In this example, an embodiment apparatus is used to determine the formation of a hexadecane thiol monolayer on a clean gold electrode. Apparatus 100 was used. The reference electrode was a Ag/AgCl reference electrode. The counter electrode was a platinum counter electrode. A gold working electrode was sealed to the bottom of the cuvette using a 0.85 mm silicone gasket. The buffer used was a standard PBS 1×. The cuvette was purged with nitrogen gas by inserting a nitrogen purge tube through a hole in the top rectangular plate. AC impedance spectroscopy was used. This is a very sensitive electrochemical measurement technique. It is used here for demonstrating the formation of a thiol monolayer on the gold working electrode. The AC impedance spectrum before and after the formation of a thiol monolayer are shown in FIG. 13. There was an increase in resistance after the formation of a thiol monolayer on the gold electrode.

EXAMPLE 3

Adsorption of Lipid Bilayers on Electrodes Using Apparatus 100

Figure 14:
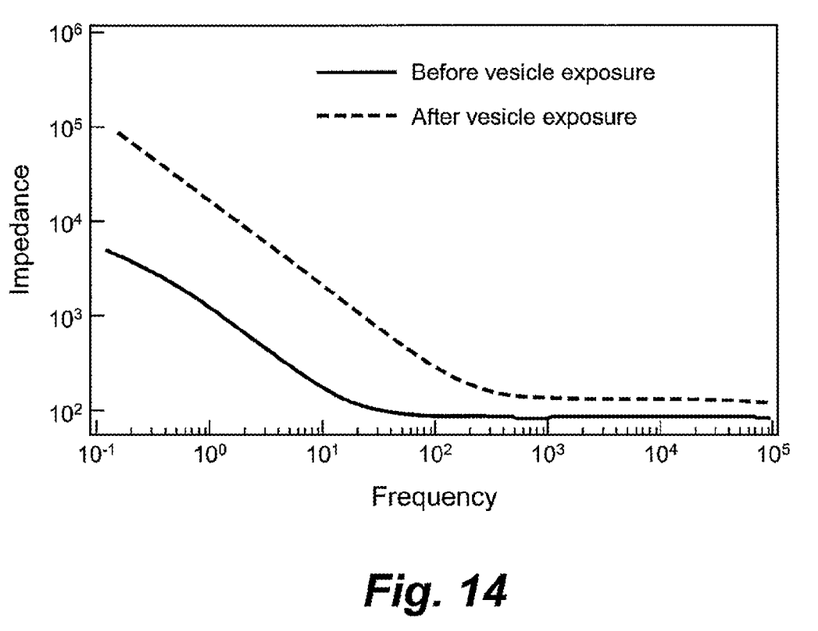
FIG. 14 shows results of formation of a lipid bilayer on an electrode surface of an embodiment apparatus.

FIG. 14 shows AC impedance data collected on a porous gold electrode using apparatus 100 before and after deposition of a lipid bilayer on the gold electrode. In this case a codeposited silicon-gold film is formed on a silicon wafer. The electrode was exposed to HF. By applying a constant potential, a porous gold electrode was formed by selectively etching silicon from the film in the electrochemical cell. The resulting electrode was exposed to lipid vesicles. FIG. 14 shows the impedance before and after adding the lipid vesicles.

EXAMPLE 4

Bulk Electrolysis

Figure 15:
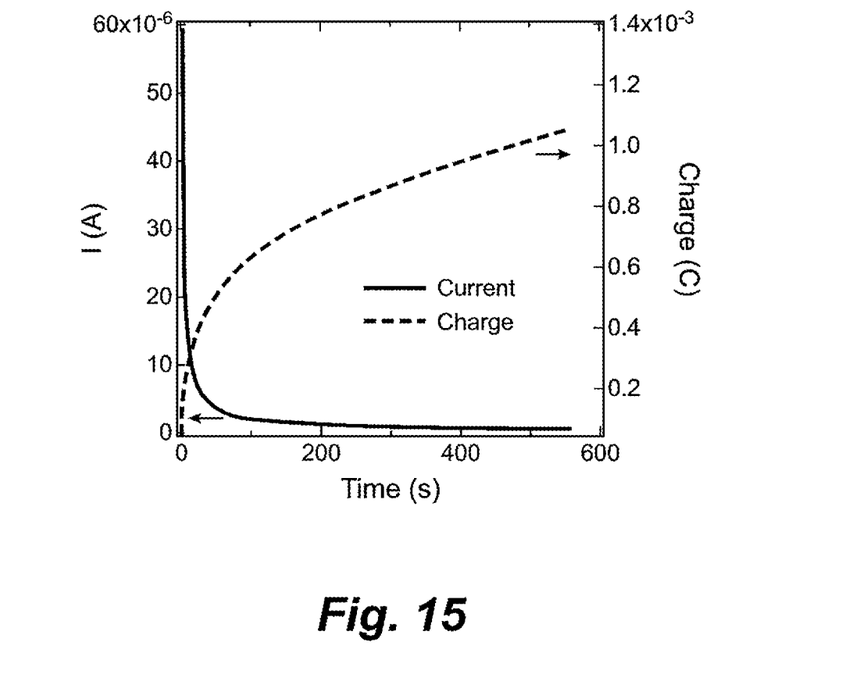
FIG. 15 shows results of a bulk electrolysis experiment using an embodiment apparatus.

In this example, the apparatus of FIG. 10a-b was used. The reference electrode 44 and the counter electrode 46 were placed in one cuvette and the working electrode in the other cuvette. A polycarbonate membrane with 0.1 micron pore size was placed in between two cuvettes, sandwiched between two silicone gaskets, and a constant potential of 0.7 V was applied on the working electrode with respect to the reference electrode. It should be understood that the reference electrode could have be placed in the same cuvette as the working electrode (Pt wire or mesh or any high surface area electrode). FIG. 15 shows a plot of current versus time at a constant potential of 0.7 V. A solution of 1 mM ferricyanide was used as an electrolyte. The ferricyanide was oxidized to ferrous cyanide over a period of time as seen by the increase in charge.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An electrochemical apparatus for analyzing a flat substrate, comprising:
    a disposable rectangular cuvette that comprises four rectangular sides, an open top end, and a bottom end with a hole therethrough,
    a flat substrate that functions as a working electrode,
    a gasket surrounding the hole in the bottom end for providing a seal in between the flat substrate that functions as a working electrode and the bottom end of the cuvette,
    a cell holder comprising a top rectangular plate having a groove that mates with said open top end of the cuvette, said groove defining a perimeter for a plurality of holes through the top plate inside the perimeter, and a bottom rectangular plate for supporting the bottom end of said cuvette, the bottom rectangular plate having four corners and a threaded hole at each corner for receiving a screw or other aligning pin for aligning the top plate with the bottom plate when the groove of the top rectangular plate mates with the open top end of the cuvette, and fastening means for fastening the bottom plate to the top plate,
    a reference electrode that fits through a hole inside the perimeter of the groove in the top rectangular plate of the cell holder and into the cuvette; and
    a counter electrode that fits through a hole inside the perimeter of the groove in the top rectangular plate of the cell holder and into the cuvette.

2. The electrochemical apparatus of claim 1, further comprising a gas purge tube that fits through a hole inside the perimeter of the groove and into the cuvette, and gas vent through another hole inside the perimeter of the groove.

3. The electrochemical apparatus of claim 1, wherein the bottom plate comprises four corners and a threaded hole at each corner for engaging a screw and wherein said top plate comprises four corners and a hole at each corner, and wherein said fastening means comprises a screw for engaging each threaded hole of the bottom plate, each screw passing through a corner hole in the top plate, and a nut for engaging each screw after each screw passes through a hole in the top plate.

4. The electrochemical apparatus of claim 1, wherein said working electrode is translucent or transparent and wherein said apparatus further comprises:
    an optical cable for sending light through the hole in the bottom plate of the cell holder, through the working electrode, and into the cuvette, and
    a spectrometer optically engaged to the fiber optic cable for receiving transmitted light from the cuvette.

5. The electrochemical apparatus of claim 1, wherein the spectrometer is chosen from a UV-Visible spectrometer, Fourier Transform Infrared spectrometer, or fluorescence spectrometer.

6. The electrochemical apparatus of claim 1, further comprising:
    a microscope objective positioned near the working electrode through the hole in the bottom plate of the cell holder aligned with the hole through the bottom of the cuvette, and
    a microscope engaged to the microscope objective.

7. The electrochemical apparatus of claim 1, wherein:
    the top rectangular plate further comprises a partition attached within the groove to the top rectangular plate, the partition extending into the rectangular cuvette to divide the cuvette into a first compartment and a second compartment without reaching the bottom end of the cuvette when the top of the cuvette mates with the groove in the top plate, and wherein the cuvette comprises two side holes in opposite rectangular sides in the first compartment for fluid flow into the first compartment and a side hole in a rectangular side in the second compartment for fluid flow out of the cuvette.

* * * * *